US006790943B1

(12) United States Patent
Broadbent et al.

(10) Patent No.: US 6,790,943 B1
(45) Date of Patent: Sep. 14, 2004

(54) REACTIVE DYE COMPOUNDS

(75) Inventors: Peter Jeffrey Broadbent, Knaresborough (GB); David Malcolm Lewis, Otley (GB); Gilles Yves Marie Fernand Genain, London (GB); Wei Dong He, Morley Leeds (GB); Taher Iqbal Yousaf, Egham (GB)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/089,340

(22) PCT Filed: Sep. 29, 2000

(86) PCT No.: PCT/US00/26975

§ 371 (c)(1),
(2), (4) Date: Mar. 27, 2002

(87) PCT Pub. No.: WO01/25338

PCT Pub. Date: Apr. 12, 2001

(30) Foreign Application Priority Data

| Oct. 1, 1999 | (GB) | 9923328 |
| Mar. 22, 2000 | (GB) | 0006969 |
| Apr. 25, 2000 | (GB) | 0009842 |

(51) Int. Cl.[7] .............................. C09B 62/78; D06F 1/38
(52) U.S. Cl. ...................... 534/617; 534/638; 534/642; 540/133; 544/189; 544/211; 552/232; 8/428; 8/524; 8/528; 8/543; 8/549
(58) Field of Search ................................ 534/617, 638, 534/642; 540/133; 544/189, 211; 552/232; 8/428, 524, 528, 543, 549

(56) References Cited

U.S. PATENT DOCUMENTS

| 3,116,275 A | 12/1963 | Gamlen et al. |
| 3,377,336 A | 4/1968 | Siegel et al. |
| 3,433,781 A | 3/1969 | Ackerman et al. |
| 3,522,246 A | 7/1970 | Siegel et al. |
| 3,527,760 A | 9/1970 | Siegel et al. |
| 3,873,513 A | 3/1975 | Kullman et al. |
| 4,092,478 A | 5/1978 | Plant et al. |
| 4,098,784 A | 7/1978 | Swidler et al. |
| 4,139,345 A | 2/1979 | Crabtree et al. |
| 4,150,021 A | 4/1979 | Swidler et al. |
| 4,832,698 A | 5/1989 | Ikeou et al. |
| 4,855,411 A | 8/1989 | Thompson et al. |
| 4,898,933 A | 2/1990 | Schläfer et al. |
| 5,037,449 A | 8/1991 | Hoegerle et al. |
| 5,175,263 A | 12/1992 | Schläfer |
| 5,548,071 A | 8/1996 | Deitz et al. |
| 5,766,267 A | 6/1998 | Schumacher et al. |
| 5,877,310 A | 3/1999 | Reddington et al. |
| 6,350,862 B1 | 2/2002 | Brock et al. |
| 6,398,822 B1 | 6/2002 | Brock et al. |
| 6,518,407 B1 | 2/2003 | Brock et al. ................ 534/604 |

FOREIGN PATENT DOCUMENTS

| CA | 771632 | 11/1967 |
| DE | 33 35 956 A1 | 4/1985 |
| DE | 196 45 601 A | 5/1998 |
| EP | 0 260 806 A2 | 3/1988 |
| EP | 0 735 107 A2 | 9/1990 |
| EP | 0 418 623 A1 | 3/1991 |
| FR | 1 274 732 A | 2/1962 |
| GB | 949 316 A | 2/1964 |
| GB | 1 020 304 | 2/1966 |
| GB | 1 060 734 | 3/1967 |
| GB | 1 275 944 | 6/1972 |
| GB | 1 414 420 A | 11/1975 |
| JP | 60 208 367 | 10/1985 |
| JP | 63 006 181 | 1/1988 |
| WO | WO 96/02593 | 2/1996 |
| WO | WO 97 19188 A | 5/1997 |
| WO | WO 99/51685 | 10/1999 |
| WO | WO 99/51686 | 10/1999 |
| WO | WO 99/51689 | 10/1999 |
| WO | WO 00/69973 | 11/2000 |
| WO | WO 00/69974 | 11/2000 |
| WO | WO 01/25336 | 4/2001 |
| WO | WO 01/25337 | 4/2001 |
| WO | WO 01/25339 | 4/2001 |

OTHER PUBLICATIONS

Stamm, Chemical Abstracts, 60:39257, 1964.*

(List continued on next page.)

*Primary Examiner*—Fiona T. Powers
(74) *Attorney, Agent, or Firm*—Jenkins, Wilson & Taylor, P.A.

(57) ABSTRACT

A reactive dye compound comprising:
(a) at least one chromophore moiety;
(b) at least one $SO_2C_2H_4$ group which is attached to the chromophore moiety either directly via the sulphur atom of the $SO_2C_2H_4$ group or via a linking group L;

characterized in that at least one $SO_2C_2H_4$ group is substituted on its terminal carbon atom with at least one Y group wherein Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal. The compounds herein have high Exhaustion Values (E), high Fixation Values (F) and high Efficiency Values (T) and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require less levels of salt for dyeing cotton substrates.

30 Claims, No Drawings

OTHER PUBLICATIONS

Grabtchev, "The Synthesis and Properties of some Triazine–stilbene Fluorescent Brighteners", Dyes Pigm., 1994, pp. 249–254, 25.

The Journal of Macromelecular Chemistry, 1976, 50, pp. 1–8, 728.

The Journal of Macromelecular Chemistry, 1977, 64, pp. 205–210, 951.

S. Horrobin, "The Hydrolysis of Some Chloro–1,3,5–Triazines", The Journal of the Chemical Society, 1963, pp. 4130–4144.

F. Lehr, "Synthesis and Application of Reactive Dyes with Heterocyclic Reactive Systems," Jan. 19, 1990, pp. 239–263.

* cited by examiner

US 6,790,943 B1

REACTIVE DYE COMPOUNDS

TECHNICAL FIELD

The present invention relates to reactive dye compounds. In particular the present invention relates to reactive dye compounds having improved dye-bath Exhaustion (E) and improved dye-fibre covalent Fixation (F).

BACKGROUND OF THE INVENTION

Reactive dye compounds are known in the art for dyeing various substrates. Such substrates include for example proteinaceous materials such as keratin, e.g. found in hair, skin and nails and various animal body parts such as horns, hooves and feathers, and other naturally occurring protein containing materials, e.g. silk and saccharide-derived materials such as those derived from. cellulose or cellulose derivatives, e.g. natural products such as cotton, and synthetic fibres such as polyamides.

Examples of classes of such reactive dyes which are well known in the art include dyes containing a vinyl sulphone group or vinyl sulphone precursor groups such as those commercially available from Dystar under the tradename Remazol.

There are many different types of commercially-available reactive dyes for dyeing cellulosic and polyamide-type substrates. However, a critical problem still facing the textile dye industry today is the significant level of dyestuff material which remains in the effluent waste water after the dyeing process is finished. The industry measure for this problem is known as dye-bath Exhaustion (E). A high Exhaustion value for a particular dye compound means that a low level of spent dye remains in the effluent after the dyeing process is complete, while a low Exhaustion value means that a high level of spent dye remains in the effluent. There is clearly a need therefore for new dye compounds which have higher Exhaustion Values compared with commercially available dye compounds, and which provide benefits in terms of reducing levels of spent dyestuff in effluent water.

As well as having a high Exhaustion Value, it is also important for a dye compound to have a high dye-fibre covalent Fixation Value (F). The Fixation Value (F) of a reactive dye compound is a measure of the extent of covalent bonding with the substrate based on the dye originally absorbed during the dyeing process. Thus 100% Fixation means that 100% of the absorbed dye covalently bonds to the substrate. Thus, there is clearly a need to provide dye compounds having increased Fixation Values. A high Fixation Value can result in a simplification of the post dyeing "soaping off process" traditionally associated with fiber reactive dye compounds. In particular, a high Fixation Value can result in a reduced time spent on the "soaping off process" together with a reduced cost.

It has now been surprisingly found that a new class of fibre reactive dye compounds derived from vinyl sulphone dyes and their precursors such as chloroethylsulphone, sulphatoethylsulphone, phosphoethylsulphone, and other blocked ethyl sulphones as known. in the art, comprising at least one chromophore group, at least one $SO_2C_2H_4$ group and at least one substituent derived from a hydrated aldehyde, a hydrated ketone, a hydrated alpha-hydroxyketone or the hydrated form of formic acid, linked via one of its oxygen atoms to the terminal carbon atom of the $SO_2C_2H_4$ group and hence forming a hemiacetal, such as for example the hydrated form of sucrose or glucose, and the hydrated form of formic acid, exhibit significantly increased values of Exhaustion (E) and Fixation (F). These dyes can be used on a wide variety of substrates. They are particularly useful for cellulosic substrates, such as cotton and/or cotton blends, and show significant improvements in terms of decreasing the amount of spent dyestuff in effluent, increasing dye affinity to the substrate, increasing the efficiency of the dye-substrate covalent reaction, and simplifying the post dyeing "soaping off process" traditionally associated with reactive dyes. In addition, the compounds of the present invention provide significantly more intense dyeings not achievable with current reactive dyes, and can be used for both high and low temperature dyeing, hence reducing the cost of the dyeing process. Furthermore, the compounds of the present invention can be used together with specific chromophores for cellulose substrate dyeing leading to significantly reduced levels of salt needed for dyeing.

SUMMARY OF THE INVENTION

According to the present invention there is provided a reactive dye compound comprising:
  (a) at least one chromophoric moiety
  (b) at least one $SO_2C_2H_4$ group which is attached to the chromophoric moiety either directly via the sulphur atom of the $SO_2C_2H_4$ group or via a linking group L;
characterised in that at least one $SO_2C_2H_4$ group is substituted on its terminal carbon atom with at least one Y group wherein Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal.

The compounds of the present invention exhibit increased Exhaustion (E), Fixation (F) and Efficiency (T) values and provide improvements in terms of reducing spent dyestuff in effluent, increasing dye affinity to the substrate, increasing the efficiency of the dye-substrate covalent reaction, ability to carry out the long-liquor dyeing process at room temperature as well as at elevated temperatures, and simplifying the post dyeing "soaping off process" traditionally associated with fiber reactive dyes. In addition, the compounds of the present invention provide significantly more intense dyeings, i.e. greater colour intensity in the dyed substrate, without compromising levelness. Typical Exhaustion Values for the compounds and products herein are greater than 95%. Typical Fixation Values for the compounds and products herein are greater than 95%.

DETAILED DESCRIPTION OF THE INVENTION

As used herein the term "reactive dye" means a dye containing one or more reactive groups, capable of forming covalent bonds with the substrate to be dyed, or a dye which forms such a reactive group in situ.

As used herein the term "Exhaustion" in relation to reactive dyes means the percentage of dye which is transferred from a solution of the dye to the substrate to be treated at the end of the dyeing process, before rinsing and soaping. Thus 100% Exhaustion means that 100% of the dye is transferred from the dye solution to the substrate.

As used herein the term "Fixation" in relation to reactive dyes means the percentage of dye which covalently bonds with the substrate, based on the dye originally absorbed during the dyeing process. Thus 100% Fixation means that 100% of the dye absorbed is covalently bonded with the substrate.

The total efficiency of reactive dyes can be measured by their Efficiency Value (T) which can be calculated from the Exhaustion Value (E) and Fixation Value (F) using the following equation:

%T=(F×E)/100

The compounds of the present invention comprise a chromophoric moiety, at least one $SO_2C_2H_4$ group linked to the chromophore group either directly via the sulphur atom or via a linking group L and at least one Y substituent wherein the Y substituent is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal.

Chromophoric Moiety

The reactive dye compounds herein can comprise one or more chromophoric moieties (D). In reactive dye compounds comprising two or more chromophoric moieties these can be the same or different. Preferably the reactive dye compounds herein comprise from one to three chromophoric moieties, preferably one or two chromophoric moieties, preferably one.

Any chromophoric moieties suitable for use for dyeing substrates can be used in the present invention. The term chromophore as used herein means any photoactive compound and includes any coloured or non-coloured light absorbing species, e.g. fluorescent brighteners, UV absorbers, IR absorbing dyes.

Suitable chromophoric moieties for use in the dye compounds herein include the radicals of monoazo, disazo or polyazo dyes or of heavy metal complex azo dyes derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye.

Suitable chromophoric moieties for use in the dye compounds herein include those disclosed in EP-A-0,735,107 (Ciba-Geigy), incorporated herein by reference, including the radicals described therein which contain substituents customary for organic dyes, such as sulphonate substituents which enhance the water solubility of the dye compound.

Most preferred chromophoric D groups for use herein are polysulphonated azo chromophores such as those present in Procion (RTM) dyes commercially available from BASF, Drimalan (RTM) dyes commercially available from Clariant, Drimarene (RTM) dyes commercially available from Clariant and Levafix (RTM), Remazol (RTM) dyes commercially available from Dystar and Sumifix supra (RTM) dyes commercially available from Sumitomo.

Substituent Y

At least one of the $SO_2C_2H_4$ groups is substituted on the terminal carbon atom with at least one Y group wherein Y is a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal.

Particularly preferred Y groups herein are derived from the hydrated forms of an aldehyde or ketone. Preferably the Y group is derived from the hydrated form of a reducing sugar selected from an aldose or a ketose.

Suitable aldose materials for use herein include an aldotriose, an aldotetrose, an aldopentose, an aldohexose, an aldohepiose and an aldooctose, and mixtures thereof. A preferred aldose material for use herein is an aldopentose material, preferably selected from ribose, xylose, arabinose, deoxyribose and fructose and mixtures thereof. Another preferred aldose material for use herein is an aldohexose material, preferably selected from glucose, galactose, talose, mannose, altrose, allose and rhamnose, and mixtures thereof. Most preferred for use herein are the hydrated forms of glucose, sucrose and fructose. Isomers of the hydrated forms of sucrose or glucose can be formed by acid hydrolysis of sucrose and glucose, respectively. A preferred Y group herein is a group derived from the hydrated form of sucrose or glucose, namely —O—$(CHOH)_4(CHOHCH_2OH)$.

Suitable ketose materials for use herein include an aldotetrulose, an aldopentulose, an aldoheptulose, an aldooctulose and mixtures thereof.

Other suitable aldehyde and ketone materials which can be converted to their hydrated form via acid hydrolysis include, but are not limited to, furfural, glucosamine, 1-glycine aldehyde, 1-mannose, 1-galactose, piperidone, 2-methylene-3-quinuclidinone dihydrate HCl, ascorbic acid, paraformaldehyde, glyoxylic acid, glyoxal, glutaraldehyde, chloral, dihydroxy tartaric acid, 2-2-dihydroxy-5-methoxy-1,5-methoxy-3-indandione hydrate (ninhydrin), 2-2-dihydroxy-1H-benz(F)indene-1,3(2H)-dione hydrate, mesoxalic acid, alloxan, pyruvic acid, glyceraldehyde, 2,5-piperazine-dione, d-erythrose, d-threose, d-ribose, d-arabinose, d-xylose, d-lyxose, d-ribulose, and the compound having the structure:

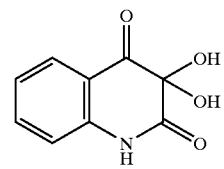

Particularly preferred Y groups herein are groups derived from saccharide molecules such as sucrose and glucose, and the like, which have been hydrolysed to their hydrated forms. A preferred Y group herein is a group derived from the hydrated isomer of sucrose or glucose, namely —O—$(CHOH)_4(CHOHCH_2OH)$. Hydrated isomers of sucrose and glucose can be formed by acid hydrolysis of sucrose and glucose, respectively. When saccharides such as sucrose and glucose are subjected to acid hydrolysis they can also form a polymeric structure and hence in that case the Y group would also be polymeric. Another preferred Y group is derived from the hydrated form of formic acid, (e.g. —CH(OH)(OH)), which can also be polymeric.

Another preferred Y group is derived from the hydrated form of formic acid (e.g. —CH(OH)(OH))

Preferred reactive dye compounds of the present invention may be represented by the following formulae (I)

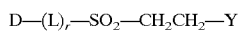

wherein:

D is a chromophore group;

r is 0 or 1, preferably 0,

L is a linking group selected from

NH, $(CH_2)_n$, N—$(CH_2)_nN$, —$(CH_2)_n$—N, NR (R is C1–C4 alkyl)

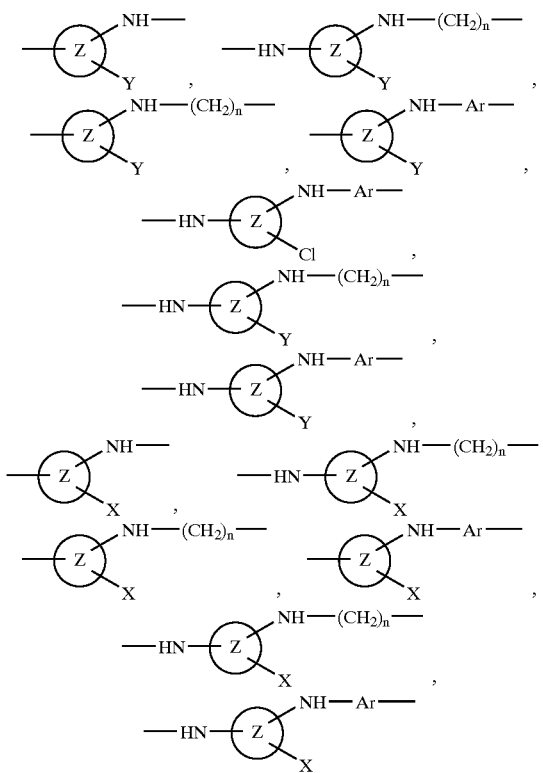

wherein Ar is an aryl group, preferably benzene, Y is as defined above, X is selected from thio-derivatives, halogen (preferably fluorine and chlorine), amines, alkoxy groups, carboxylic acid groups, CN, $N_3$, quaternized nitrogen derivatives, Q+, and oxy- or thiocarbonyl derivatives having the formula —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same of different and may be selected from $C_1$–$C_4$ alkyl; Z is a nitrogen-containing heterocycle, n is an integer of from 1 to 4; and salts thereof.

When the starting dye compound has multiple reactive groups, for example two reactive groups, one can substitute, for example, one or both of these reactive groups by one or two Y groups, wherein two Y groups in the same molecule may be the same or different.

Particularly preferred reactive dye compounds herein have the structure I(a) below:

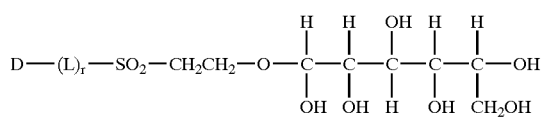

wherein D, L, and r are as defined above.

An especially preferred reactive dye compound herein has the following structure (Ib)

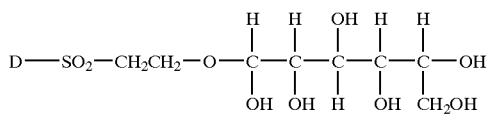

wherein D is as defined above.

Compounds having the structure Ib above can be obtained by using a vinyl sulphone dye as the starting dye, such as for example, Remazol Red RB, Remazol Yellow 3RS, Remazol Turquoise Blue G, and reacting it with a compound containing a Y group such as for example the hydrated forms of sucrose, glucose and formic acid.

Another preferred reactive dye compound herein has the structure (Ic) below:

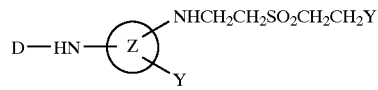

wherein D, Y are as defined above and Z is a nitrogen-containing heterocycle as defined below. Examples of compounds having the structure (Ic) above can be obtained by using as the starting dye, a dye containing both vinyl sulphone and nitrogen-containing heterocycle functional groups, such as for example, Cibacron Red C2G, Cibacron Yellow C2R and Cibacron Blue CR. These starting dyes are reacted with compounds containing a suitable Y group, such as for example, the hydrated form of glucose, sucrose or formic acid.

Yet another preferred reactive dye compound herein has the structure (Id) below:

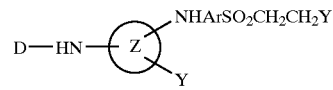

wherein D, Ar, and Y are as defined above and Z is a nitrogen-containing heterocycle as defined below. Examples of compounds having the structure (Id) above can be obtained by using as the starting dye, a dye containing both vinyl sulphone and nitrogen-containing heterocycle functional groups, and an additional benzene group as part of the L linking group, such as for example, Sumifix Supra Red 2BF and Sumifix Supra Yellow 3RF. These starting dyes are reacted with compounds containing a suitable Y group, such as for example, the hydrated form of glucose, sucrose or formic acid.

The Y group may also exist in a polymeric form due to a polymer being formed when the reducing sugar or formic acid is hydrolysed with acid.

Nitropen-containing Heterocycle (Z)

Suitable nitrogen containing heterocycles for use herein include monocyclic, bicyclic or polycyclic, unsaturated heterocycles containing at least one nitrogen heteroatom. When monocyclic rings are used, they arc preferably selected from unsaturated rings having from about 3 to about 7 ring atoms, especially 5 or 6 ring atoms, comprising from about 1 to about 3 nitrogen heteroatoms, preferably 2 or 3 nitrogen heteroatoms. When bicyclic heterocycles are used, they preferably comprise an unsaturated nitrogen containing heterocycle having 3 to 7 ring atoms, preferably an unsaturated nitrogen containing heterocycle having 5 or 6 ring atoms comprising 1 or 2 nitrogen atoms, fused to a 5 to 7 membered carbocycle preferably a 6-membered unsaturated carbocycle. When bicyclic heterocycles are used, the oxy carbonyl substituents are preferably attached to the nitrogen containing heterocyclic ring.

Preferred for use herein are 5 or 6 membered unsaturated nitrogen containing monocyclic heterocyclic rings comprising 2 or 3 nitrogen heteroatoms or bicyclic rings containing a 5 or 6 membered unsaturated heterocyclic ring containing 2 nitrogen heteroatoms fused to a 6 membered unsaturated carbocycle.

Examples of suitable heterocycles for use herein include, but are not necessarily limited to triazine, pyrimidine, quinoxaline, pyrimidinone, phthalazine, pyridazone and pyrazine.

Preferred for use in the compounds herein are triazine, pyrimidine and quinoxaline.

The present invention further relates to processes for the preparation of dyes herein. In general, dyes herein are prepared by a process which comprises the steps of reacting a first starting material (preferably one mole) with a second starting material (preferably one mole), the first starting material comprising at least one chromophore, at least one $SO_2C_2H_4$ group which is attached to the chromophore group either directly via the sulphur atom of the $SO_2C_2H_4$ group or via a linking group (for example a Remazol dye), the second starting material being a compound containing a suitable Y group, such as for example the hydrated form of a saccharide material such as sucrose or glucose, or the hydrated form of formic acid. As described above, the hydrated form of the saccharide material is preferably obtained via acid hydrolysis. However there are other ways to obtain the hydrated form, for example, those hydrated aldehydes or ketones which are naturally occuring, e.g. 4-piperidone hydrate. It is preferable that the reaction is carried out at a pH of between 2 to 8, preferably 3 to 5 and over several hours, preferably 1 to 5 hours, more preferably 2–3 hours.

Compounds herein having the formula (1) are preferably prepared by reacting a first starting material (preferably one mole) with a second starting material (preferably one mole), the first starting material containing a D-(L)$_r$—SO$_2$—CH$_2$CH$_2$—group as defined above (for example a Remazol dye, such as Remazol Brill Blue RS commercially available from Dystar), the second starting material being compound containing a Y group such as the hydrated form of a saccharide molecule such as sucrose and glucose. It is preferable that the reaction is carried out over several hours (2–5 hours). It is also important to add the saccharide dropwise over several hours, preferably from about 1 to about 5 hours, preferably from about 1 to about 3 hours.

The person skilled in the art will appreciate that there are other processes which may be used for manufacturing the compounds and products according to the present invention. Alternative preparation processes include, but are not limited to:

(i) Diazotising the in situ fofned sulphate ester of the hydroxy ethyl sulphone and then coupling this onto a suitable coupling component as in the following reactions:

Reaction 1:

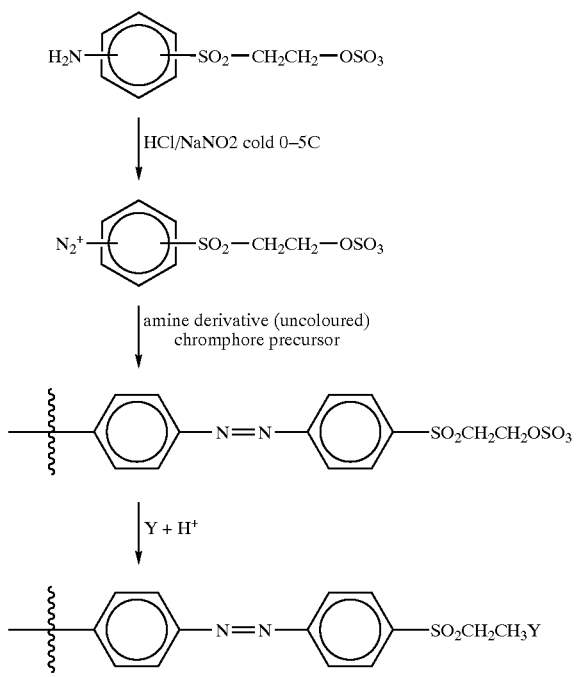

Reaction 2:

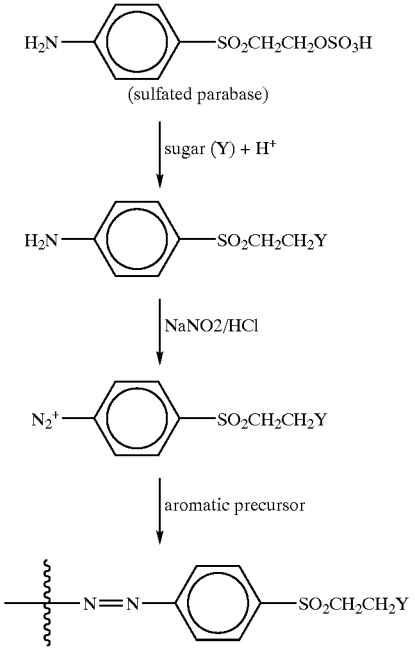

Reaction 3:

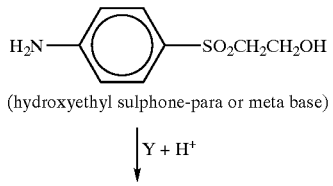

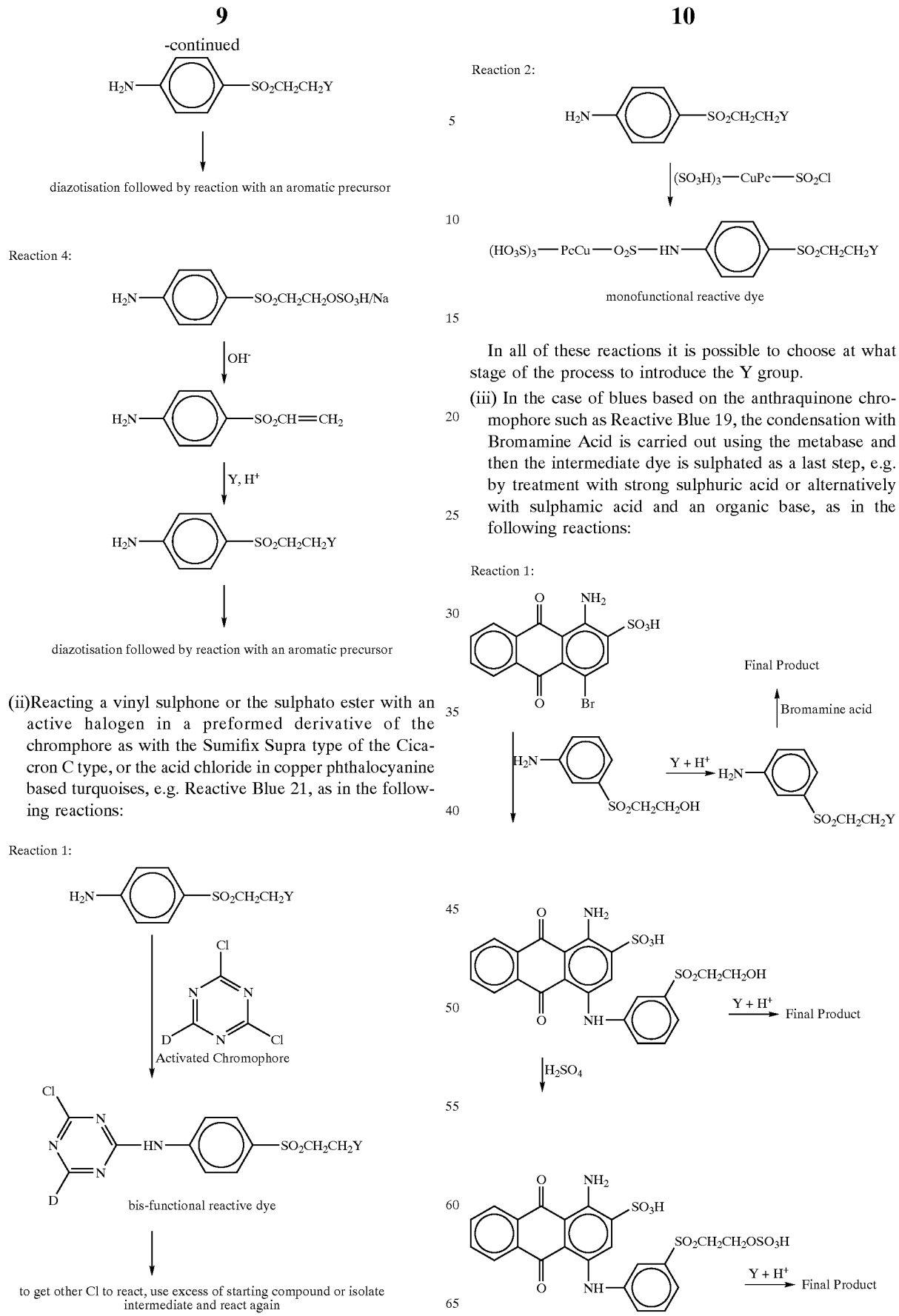

In all of these reactions it is possible to choose at what stage of the process to introduce the Y group.

(iii) In the case of blues based on the anthraquinone chromophore such as Reactive Blue 19, the condensation with Bromamine Acid is carried out using the metabase and then the intermediate dye is sulphated as a last step, e.g. by treatment with strong sulphuric acid or alternatively with sulphamic acid and an organic base, as in the following reactions:

(ii) Reacting a vinyl sulphone or the sulphato ester with an active halogen in a preformed derivative of the chromphore as with the Sumifix Supra type of the Cicacron C type, or the acid chloride in copper phthalocyanine based turquoises, e.g. Reactive Blue 21, as in the following reactions:

Reaction 2:

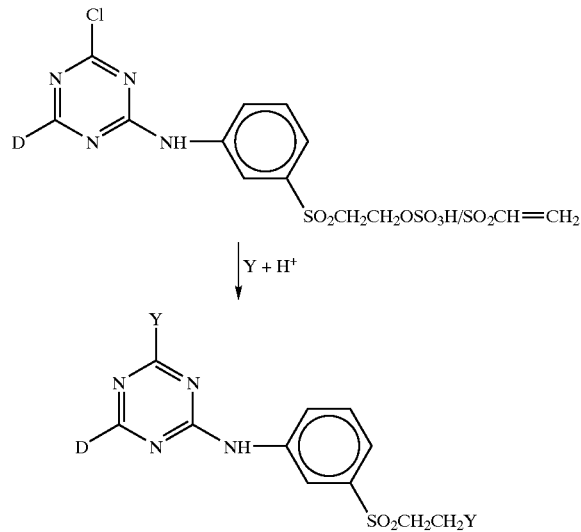

Depending upon the reaction conditions (for example, amounts of each starting material, form of each starting material), mixtures of different dye compounds may be obtained in the final product, such mixtures containing for example, products formed from further substitution reactions, structural isomers and the like.

Hence according to another aspect of the present invention there is provided the product obtainable by any of the processes detailed herein.

In particular, there is provided a product obtainable by a process wherein the process comprises the steps of reacting a first starting material (preferably one mole) with a second starting material (preferably one mole), the first starting material comprising at least one chromophore, at least one $SO_2C_2H_4$ which is attached to the chromophore group either directly via the sulphur atom of the $SO_2C_2H_4$ group or via a linking group L (for example a Remazol dye), the second starting material being a compound containing a suitable Y group, such as for example, the hydrated form of a saccharide material, preferably sucrose or glucose. It is preferable that the reaction is carried out at a pH of between 2 to 8, preferably 3 to 5 and over several hours, preferably 1 to 5 hours, more preferably 2–3 hours.

It is also preferable that the saccharide material is converted to its hydrated form before being reacted with the first starting material. This is preferably done by acid hydrolysis of the saccharide material.

The dye compounds herein are suitable for dyeing and printing a wide variety of substrates, such as silk, leather, wool, polyamide fibers and polyurethanes, keratin fibres such as hair, and in particular cellulosic materials, such as the natural cellulose fibres, cotton, linen, hemp and the like, paper, and also cellulose itself and regenerated cellulose, and hydroxyl-containing fibres contained in blend fabrics, for example blends of cotton with polyester or polyamide fibres.

The dye compounds of the present invention can be applied and fixed to the substrate in various ways, in particular in the form of a solid mixture, aqueous dye solutions and printing pastes. Thus according to the present invention there is provided a dye composition comprising one or more of the dye compounds described herein together with any carrier material suitable for use in a dye composition.

Preferred dye compositions herein comprise an acidic or neutral buffer material. Any acidic buffer suitable for use in dye compositions can be used herein. An example of a suitable buffer is a mixed phosphate buffer.

When the dye composition herein is in the form of a paste a preferred ingredient is a thickening agent. Any suitable thickening agents suitable for use in reactive dye compositions can be used herein.

When the dye composition is in the form of an aqueous solution or aqueous gel/paste, the dye composition preferably has a pH of from about 2 to about 8. When acidic buffers are used the dye composition preferably has a pH of from about 2 to about 5, especially from about 2 to about 3. When neutral buffers are used, the dye composition preferably has a pH of from about 4 to about 8, preferably from about 6 to about 8.

The dyeing and printing processes which can be used with the dyes herein are conventional processes which are well known and which have been widely described in the technical and patent literature. The dye compounds herein are suitable for dyeing both by the exhaust method (long liquor) and also by the pad-dyeing method, whereby the goods are impregnated with aqueous, salt-containing or salt-free dye solutions and the dye is fixed after an alkali treatment or in the presence of alkali, if appropriate with the application of heat. The dye compounds herein are also suitable for the cold pad-batch method, after which the dye together with the alkali is applied using a pad-mangle, the fabric batched on a roll. A dye-fibre covalent reaction occurs over several hours of storage at room temperature. Alternatively, padded or printed goods may be fixed by a steaming process using steam temperatures between 100–130° C. After fixing, the dyeings or prints are thoroughly rinsed with cold and hot water, if appropriate with the addition of an agent acting as a dispersant and promoting the diffusion of the non-fixed portions.

For cotton blends, a preferred dyeing process is as follows. A mixture of dyes is prepared comprising dyes according to the present invention together with direct dyes. The reactive dyes are fixed at a temperature of 100° C. and the direct dyes are fixed at a temperature of 130° C. Uniform dyeing of the cotton blend is obtained.

Thus in accordance with another aspect of the present invention there is provided a use of the reactive dyes of the present invention for dyeing and printing substrates such as cotton, wool, nylon, silk, keratin, hair, leather, paper and the like. The compounds herein can be used in methods of dyeing all of the substrates listed above by applying an aqueous solution of one or more of the reactive dyes of the present invention to the substrate to be dyed under suitable conditions of pH and temperature.

The following examples serve to illustrate the compounds and compositions of the present invention.

The starting compounds and components given in the examples below can be used in the form of the free acid or in the form of their salts. As discussed above, the products obtained in the examples below may comprise mixtures of different dye compounds. In the Examples below all the starting materials are commercially available. In particular the Remazol dyes are available from Dystar Textilfarben, GmbH & Co., Deutschland KG, BU-R/F & E, Werk Hoechst, Building G834, D-65926 Frankfurt am Main, Germany, and the Sumifix dyes are available from Sumitomo Chemical Co. Ltd., 3-1-98, Kasugade-naka, Konohana-ku, Osaka 554, Japan. The Cibacron dyes are available from Ciba, Basle.

EXAMPLES

The reactive dye compounds of the present examples are prepared as follows. Xg of pure Starting Dye is dissolved in 150 ml of distilled water in a 400 ml flask. The temperature of the reaction system is adjusted and maintained at y° C. The pH of the starting dye solution is adjusted to z using solid sodium carbonate. Ag of sugar is dissolved in 50 ml of distilled water. The pH of this sugar solution is adjusted to b and the sugar acid hydrolysis continues at ambient temperature for 30–35 minutes as shown below.

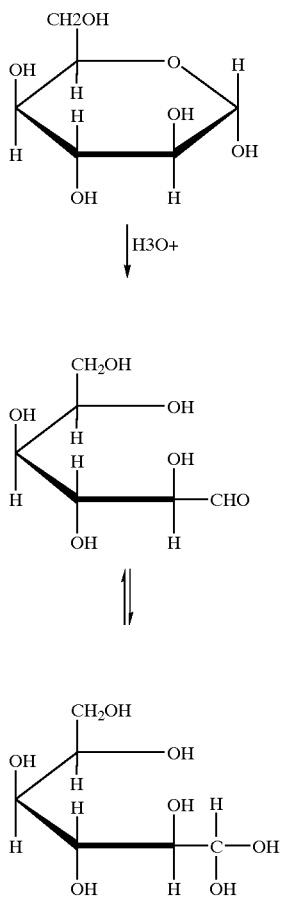

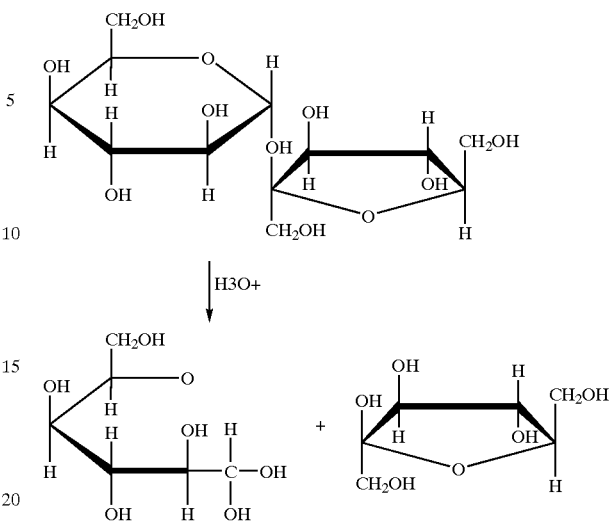

Acid Hydrolysis of Sucrose

The hydrolysed sugar solution is slowly added into the solution of starting dye. The rate of addition is such that the addition takes around c hours to complete. During the process of addition the temperature of the reaction system is maintained at d° C. After addition of the sugar solution is complete, the reaction is allowed to continue for e hours. The endpoint of the reaction is indicated by the pH of the reaction system remaining constant for more than 5 minutes. At this point the final dye is obtained. Using 6N HCl, the pH of the system is then reduced to below 2.5 to terminate the reaction. KSCN (about 25% of the total solution) is then added to the reaction mixture in order to precipitate the dye product. Filtration using Whatman filter paper is then carried out. The precipitate is then washed with acetone for 5–6 times (about 50 ml of acetone used each time) to obtain the final dye product in fine powder form offcolour. Table I displays Examples 1 to 16 together with reaction conditions y,z,b.c,d and e, amounts of material x and a, colour of final product f, Starting Dye, Final Dye and type of sugar.

A possible synthetic mechanism for the reaction of the Cibacron dyes with glucose in its hydrated form is as follows:

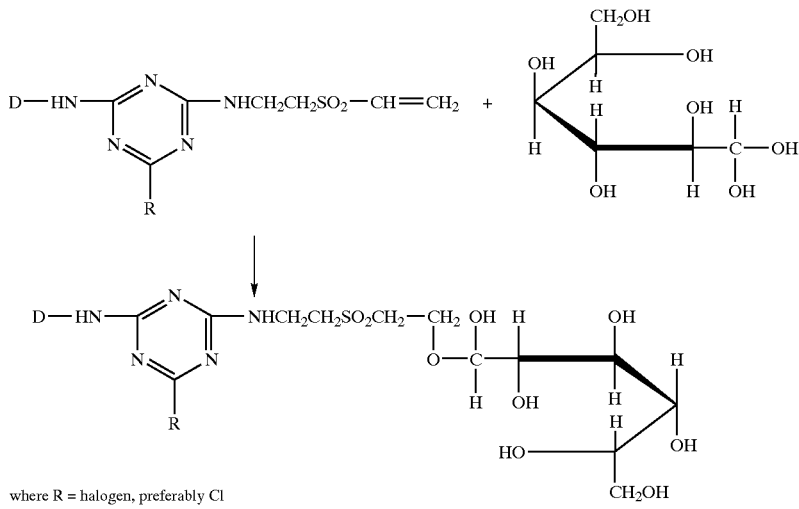

where R = halogen, preferably Cl

It is also possible to carry out further reactions to obtain a bis-stucture.

A possible synthetic mechanism for the reaction of the Sumifix dyes with glucose in its hydrated form is as follows:

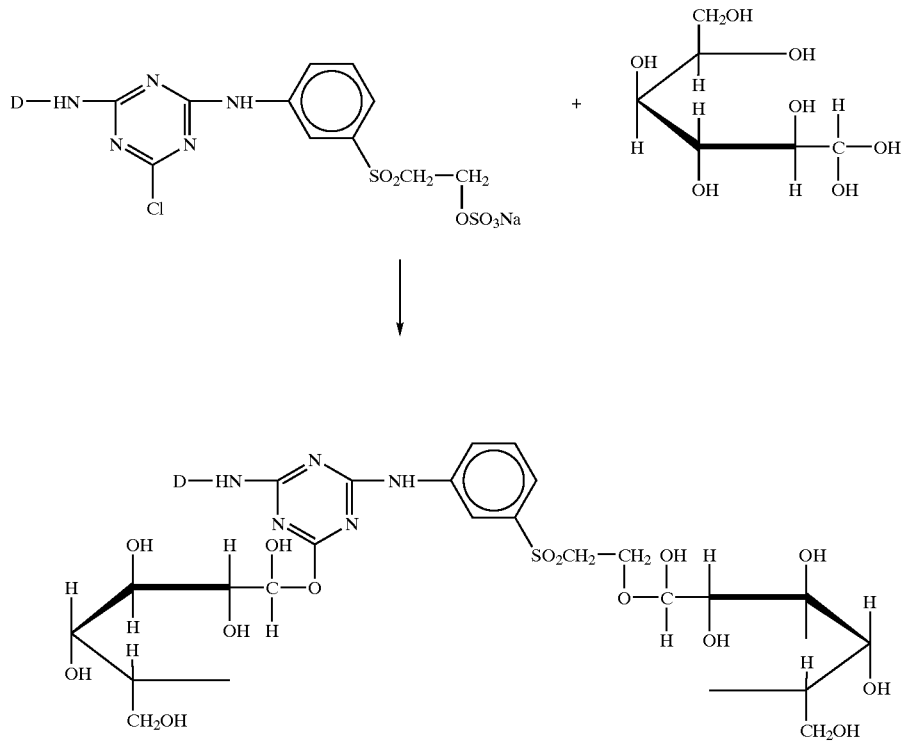

If an excess of starting dye is used it is possible to get bis-structures in the final product.

The compounds prepaced according to Examples 1 to 16 and at standard depths all have high Exhaustion Values, high Fixation Values, particularly on cellulosic substrates such as cotton, and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require less levels of salt for dyeing cotton substrates. These advantages can be demonstrated by the following Examples 17 and 18.

Example 17

All dye compounds prepared according to Examples 1 to 16 can be used to dye cotton using the dyeing procedures detailed below. After the cotton dyeing procedure has been carried out a soaping-off process can also be carried out on the cotton fibre.

Cotton Dyeing Procedure

An aqueous dye solution is prepared containing a dye compound according to any of Examples 1 to 16. The dye solution contains 1% on mass of fibre of dye, 80 g/L $Na_2SO_4$ and 5% on mass of fibre of sodium acetate. The cotton fabrics are soaked in water and then the cotton fabrics are dyed in the above dye-bath at pH 7 at 50° C. for 15 minutes. The dyed cotton fabric is then fixed in the dye-bath at pH 11.5 with addition of 30 g/L of trisodium phosphate and dyeing continued at 50° C. for 45 minutes. The dyed fabric is rinsed with water.

In the above dyeing procedure the dye bath for each dye compound is almost totally exhausted (i.e. only slight colour in the dye bath after dyeing), indicating that the compounds prepared according to Examples 1 to 16 each have a high Exhaustion Value (typically >95%). The Exhaustion Values for each product can be obtained by comparing the photo-absorption of the dyebath liquid before and after dyeing. The Exhaustion Values for Examples 1 to 16 are given in Table A below.

Soapin-off Process

A soaping off process can then be carried out by washing the dyed fabrics with an aqueous solution of Sandozine NIE (2 g/L) (available from Clariant (Switzerland) Ltd., R&D Dyestuffs, Post Box, Building 88/1007, CH-4002 Basel) at 100° C. for 30 minutes.

In the above soaping-off process hardly any colour was removed from the fabric, resulting in an almost colourless soaping liquid, indicating that the compounds prepared according to Examples 1 to 16 each have a high degree of dye-fibre covalent bonding and a high Fixation Value (typically >95%). The Fixation Values of the dye products prepared according to Examples 1 to 16 are shown in Table A below.

From the Exhaustion and Fixation Values, the Efficiency Values for each dye product can be calculated.

TABLE A

Exhaustion, Fixation and Efficiency Values for the dye products of Examples 1 to 16

| Eg. | Exhaustion Value (E %) | Fixation Value (F %) | Efficiency Value (T) |
|---|---|---|---|
| 1 | 97.32% | 97.21% | 94.61 |
| 2 | 98.90% | 97.05% | 95.98 |
| 3 | 97.27% | 96.07% | 93.45 |
| 4 | 98.68% | 98.27% | 96.98 |
| 5 | 98.71% | 97.99% | 96.72 |
| 6 | 98.71% | 97.99% | 96.72 |
| 7 | 97.62% | >95% | >90 |
| 8 | 97.62% | 99.62% | 97.24 |
| 9 | 98.19% | 99.01% | 97.21 |
| 10 | 99.12% | 97.75% | 96.88 |
| 11 | 96.51% | 99.45% | 95.98 |
| 12 | 98.28% | 98.39% | 96.98 |
| 13 | 98.90% | 98.73% | 97.64 |
| 14 | 97.95% | 97.26% | 95.27 |
| 15 | 99.62% | 98.24% | 97.86 |
| 16 | 97.72% | 98.47% | 96.25 |

The E, F and T values of the dyes according to the present invention are typically higher than many of the commercially available starting materials. In particular, the F and T values of the dyes according to the present invention are significantly higher than those of the commercially available starting materials.

Co3 (International Standards Organisation) Wash Fastness Test

The dyed fabrics are washed with an aqueous solution containing ECE Reference Detergent (5 g/ml) and sodium carbonate (2 g/ml) at 60° C. for 30 minutes.

In the above wash fastness test, no noticeable colour was removed from the cotton fibre and no staining of the white adjacent fibres occurred (using Multiple Fibre adjacent strip supplied by the Society of Dyes and Colourists, Bradford, UK).

Example 20

All dye compounds prepared according to Examples 1 to 16 can be used to dye nylon or wool using the dyeing procedures detailed below. After the nylon/wool dyeing procedure has been carried out a wash-test procedure can be carried out on the dyed fabric to test the wash-fastness of the dye compounds.

Wool/Nylon Dyeing Procedure

The wool/nylon fabric is soaked in a 2% w/w Alcopol-O (40% w/w sodium-d-isooctylsulpho-succinate commercially available from Allied Colloids) solution. The fabric is then dyed for 1 hour at 100° C. and pH 3.5 in a dye-bath containing the following compositions: 1.2% on mass of fibre of dye prepared according to any of Examples 1 to 7,5% on mass of fibre of sodium acetate, 1% Albegal B (commercially available from Ciba). The dyed wool/nylon fabric was then rinsed with water.

In the above procedure intense dyeings are provided for each of the compounds prepared according to Examples 1 to 16.

Co2 (ISO) Wash Fastness Test Procedure for Wool/Nylon Fabrics

The dyed wool/nylon fabric is washed in an aqueous solution containing 5 g/L of ECE Reference Detergent (commercially available from the Society of Dyers and Colourists, Bradford, UK) at 50° C. for 45 minutes.

In the above wash fastness test, no noticeable colour was removed from the wool fibre and no staining of the white adjacent fibres occurred ((using multiple fibre adjacent strip supplied by sdc bradford)

TABLE A

| Eg | Starting Dye | Sugar | x | y | z | a | b | c | d | e | Final Dye | f |
|---|---|---|---|---|---|---|---|---|---|---|---|---|
| 1 | Remazol Red RB | Glucose | 4 g | 35–40° C. | 4–5 | 1.2 g | <pH 2 | 3–3.5 hr | 35–40° C. | 1–2 hrs | Remazol Red RB/Glu | Deep Red |
| 2 | Remazol Yellow 3RS | Glucose | 4 g | 30–35° C. | 3.5–4.5 | 1.2 g | <pH 2 | 2.5–3 hr | 30–55° C. | 1–1.5 hrs | Remazol Yellow 3RS/Glu | Yellow |
| 3 | Remazol Turquoise Blue G | Glucose | 4 g | 40–45° C. | 4–5 | 1.2 g | <pH 2 | 3–4 hrs | 40–45° C. | 1–1.5 hrs | Remazol Turquoise Blue G/Glu | Turquoise Blue |
| 4 | Remazol Brill Blue R Special | Glucose | 4 g | 35–40° C. | 4.5–5.5 | 1.2 g | <pH 2 | 3–3.5 hrs | 35–40° C. | 1–1.5 hrs | Remazol Brill Blue R Special/Glu | Deep Blue |
| 5 | Cibacron Red C2G | Glucose | 4 g | 25–30° C. | 4–4.5 | 1.2 g | <pH 2 | 3–4 hrs | 25–30° C. | 2–3 hrs | Cibacron Red C2G/Glu | Deep Red |
| 6 | Cibacron Yellow C2R | Glucose | 4 g | 30–35° C. | 4–4.5 | 1.2 g | <pH 2 | 3–3.5 hrs | 30–35° C. | 2–3 hrs | Cibacron Yellow C2R/Glu | Yellow |
| 7 | Cibacron Blue CR | Glucose | 4 g | 30–35° C. | 4–4.5 | 1.2 g | <pH 2 | 3–4 hrs | 30–35° C. | 2–3 hrs | Cibacron Blue CR/Glu | Deep Blue |
| 8 | Sumifix Supra Red | Glucose | 4 g | 40–45° C. | 4.2–4.8 | 1.2 g | <pH 2 | 3–4 hrs | 40–45° C. | 2–3 hrs | Sumifix Supra Red 2BF/Glu | Deep Red |

TABLE A-continued

| Eg | Starting Dye | Sugar | X | Y | Z | A | B | C | D | E | Final Dye | F |
|---|---|---|---|---|---|---|---|---|---|---|---|---|
| 9 | Sumifix Supra Yellow 3RF | Glucose | 4 g | 40–45° C. | 4–4.5 | 1.2 g | <pH 2 | 3–4 hrs | 40–45° C. | 2–3 hrs | Sumifix Supra Yellow 3RF/Glu | Yellow |
| 10 | Sumifix Supra Blue BRF | Glucose | 4 g | 40–45° C. | 4.2–4.8 | 1.2 g | <pH 2 | 3–4 hrs | 40–45° C. | 2–3 hrs | Sumifix Supra Blue BRF/Glu | Blue |
| 11 | Sumifix Supra Turquoise BGF | Glucose | 4 g | 40–45° C. | 3.5–4.2 | 1.2 g | <pH 2 | 3–4 hrs | 40–45° C. | 2–3 hrs | Sumifix Supra Turquoise BGF/Glu | Turquoise |
| 12 | Remazol Red RB | Sucrose | 4 g | 40–45° C. | 4.5–5.5 | 1 g | pH 2.5 | 3–4 hrs | 40–45° C. | 1–2 hrs | Remazol Red RB/SG | Deep Red |
| 13 | Remazol Yellow 3RS | Sucrose | 4 g | 40–45° C. | 4.5–5.5 | 1 g | pH 2.5 | 3–4 hrs | 40–45° C. | 1–1.5 hrs | Remazol Yellow 3RS/SG | Yellow |
| 14 | Remazol Turquoise Blue G | Sucrose | 4 g | 40–45° C. | 4–5 | 1 g | pH 2.5 | 4–5 hrs | 40–45° C. | 1–1.5 hrs | Remazol Turquoise Blue G/SG | Deep Blue |
| 15 | Remazol Brill Blue R Special | Sucrose | 4 g | 45–50° C. | 4–4.5 | 1 g | pH 2.5 | 4–5 hrs | 40–45° C. | 1–2 hrs | Remazol Brill Blue R Special/SG | Deep Blue |
| 16 | Remazol Red RB | Formic Acid | 4 g | 20–22° C. | 4.5–5.5 | 1 g | pH 3–3.5 | 3–4 hrs | 20–22° C. | 1–1.5 hrs | Remazol Red RB/SG | Deep Red |

What is claimed is:

1. A reactive dye compound comprising:
   (a) at least one chromophore moiety;
   (b) at least one SO2C2H4 group which is attached to the chromophore moiety either directly via the sulphur atom of the SO2C2H4 group or via a linking group L;
characterised in that at least one SO2C2H4 group is substituted on its terminal carbon atom with at least one Y group wherein Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal.

2. A reactive dye compound according to claim 1 wherein Y is derived from a hydrated aldehyde or ketone or the hydrated form of formic acid.

3. A reactive dye compound according to claim 1 wherein Y is derived from the hydrated form of a reducing sugar selected from an aldose or a ketose, or the hydrated form of formic acid.

4. A reactive dye compound according to claim 3 wherein said aldose is selected from an aldotriose, an aldotetrose, an aldopentose, an aldohexose, an aldoheptose and an aldooctose, and mixtures thereof.

5. A reactive dye compound according to claim 4 wherein said aldose is an aldopentose selected from ribose, xylose, arabinose, deoxyribose and fructose, and mixtures thereof.

6. A reactive dye compound according to claim 5 wherein said aldose is an aldohexose selected from glucose, galactose, talose, mannose, altrose, allose and rhamnose, and mixtures thereof.

7. A reactive dye compound according to claim 1 wherein Y is derived from glucose, sucrose or fructose or the hydrated form of formic acid.

8. A reactive dye compound according to claim 3 wherein said ketose is selected from an aldotetrulose, an aldopentulose, an aldohexulose, an aldoheptulose, and an aldooctulose, and mixtures thereof.

9. A reactive dye compound according to claim 1 wherein Y is —O—(CHOH)4(CHOHCH2OH).

10. A reactive dye compound having the structure:

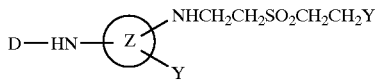

wherein D is a chromophore group; Z is a nitrogen-containinq heterocycle; and Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal.

11. A reactive dye compound having the structure:

wherein D is a chromophore group; Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ qroup thereby forming a hemiacetal; and Ar is an arvi group, preferably benzene.

12. A method of dyeing a cellulosic substrate, comprising contacting the cellulosic substrate, with a compound according to claim 1.

13. A method of dyeing wool, comprising contacting the wool with a compound according to claim 1.

14. A method of dyeing a polyamide substrate, preferably nylon, comprising contacting the polyamide substrate with a compound according to claim 1.

15. A method of dyeing silk, comprising contacting the silk with a compound according to claim 1.

16. A method of dyeing keratin, comprising contacting the keratin with a compound according to claim 1.

17. A method of dyeing leather, comprising contacting the leather with a compound according to claim 1.

18. Process for the preparation of a compound according to claim 1 comprising the steps of reacting a first starting material with a second starting material, the first starting material comprising at least one chromophore and at least one $SO_2C_2H_4$ group which is attached to the chromophore group either directly via the sulphur atom of the $SO_2C_2H_4$ group or via a linking group, the second starting material being a compound containing a suitable Y group.

19. Process according to claim 18 wherein the reducing sugar is selected from sucrose, glucose and mixtures thereof.

20. Process according to claim 18 wherein the process is carried out at a pH of from about 2 to about 8.

21. Process according to claim 18 wherein the second starting material is added to the first starting material slowly.

22. Product obtainable by the process according to claim 18.

23. A dye composition comprising the compound of claim 1 or the product of claim 18.

24. A dye composition according to claim 23 wherein the composition is in the form of a solid mixture and further comprises an acidic or neutral buffer.

25. A dye composition according to claim 23 wherein the composition is in the form of a liquid and further comprises water and an acidic or neutral buffer.

26. A dye composition according to claim 23 wherein the composition is in the form of a paste and further comprises water, thickening agent and an acidic or neutral buffer.

27. A dye composition according to claim 23 wherein the pH of the composition is in the range of from about 2 to about 5, when an acidic buffer is present, and in the range of from about 4 to about 8 when a neutral buffer is present.

28. A reactive dye compound having the formula (I):

$$D-(L)_r-SO_2-CH_2CH_2-Y$$

wherein:
D is a chromophore group;
r is 0 or 1
L is a linking group selected from:
NH, $(CH_2)_n$, $N-(CH_2)_nN$, $-(CH_2)_n-N$, NR (R is C1–C4 alkyl)

[structures with Z rings bearing substituents NH—, NH—(CH2)n—, NH—Ar—, and Y, Cl, or X groups]

wherein Ar is an aryl group, preferably benzene, Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal, X is selected from halogen (preferably fluorine and chlorine), amines, alkoxy groups, carboxylic acid groups, CN, $N_3$, and oxy- or thio-carbonyl derivatives having the formula —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same or different and may be selected from $C_1$–$C_4$ alkyl; Z is selected from triazine, pyrimidine, quinoxaline, pyrimidinone, phthalazine, pyridazone and pyrazine; n is an integer of from 1 to 4; and salts thereof.

29. A reactive dye compound having the formula (I):

$$D-(L)_r-SO_2-CH_2CH_2-Y$$

wherein:
D is a chromophore group;
r is 0
L is a linking group selected from:
NH, $(CH_2)_n$, $N-(CH_2)_nN$, $-(CH_2)_n-N$, NR (R is C1–C4 alkyl)

[structures with Z rings bearing substituents NH—, NH—(CH2)n—, NH—Ar—, and Y, Cl, or X groups]

wherein Ar is an aryl group, preferably benzene, Y is derived from a hydrated aldehyde, a hydrated ketone, a hydrated alpha-hydroxy ketone or the hydrated form of formic acid, and linked via one of its oxygen atoms to the terminal carbon of the $SO_2C_2H_4$ group thereby forming a hemiacetal, X is selected from halogen (preferably fluorine and chlorine), amines, alkoxy groups, carboxylic acid groups, CN, $N_3$, and oxy- or thio-carbonyl derivatives having the formula —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same or different and may be selected from $C_1$–$C_4$ alkyl; Z is a nitrogen-containing heterocycle; n is an integer of from 1 to 4;

and salts thereof.

30. A reactive dye compound having the formula (I):

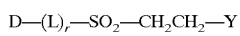

D—(L)$_r$—$SO_2$—$CH_2CH_2$—Y wherein:

D is a chromophore group;

r is 0 or 1

L is a linking group selected from:

NH, $(CH_2)_n$, N—$(CH_2)_n$N, —$(CH_2)_n$—N, NR (R is C1–C4 alkyl)

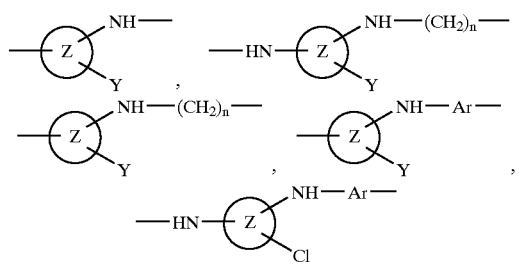

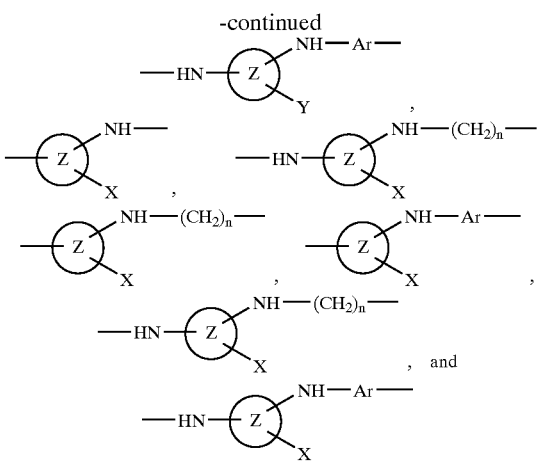

wherein Ar is an aryl group, preferably benzene, Y is as defined above, X is selected from halogen (preferably fluorine and chlorine), amines, alkoxy groups, carboxylic acid groups, CN, $N_3$, and oxy- or thio-carbonyl derivatives having the formula —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same or different and may be selected from $C_1$–$C_4$ alkyl; Z is a nitrogen-containing heterocycle; n is an integer of from 1 to 4; and salts thereof.

* * * * *